US011253557B2

(12) United States Patent
Shaw et al.

(10) Patent No.: US 11,253,557 B2
(45) Date of Patent: Feb. 22, 2022

(54) THERAPEUTIC BACTERIOPHAGE COMPOSITIONS

(71) Applicant: Armata Pharmaceuticals, Inc., Marina del Rey, CA (US)

(72) Inventors: Karen Joy Shaw, Glen Allen, VA (US); Sandra P. Morales, Sydney (AU); Gillian Mearns, Sydney (AU); Deborah A. Rankin, Sydney (AU); Frenk Smrekar, Ljubjlana (SI)

(73) Assignee: ARMATA PHARMACEUTICALS, INC., Marina del Rey, CA (US)

( * ) Notice: Subject to any disclaimer, the term of this patent is extended or adjusted under 35 U.S.C. 154(b) by 117 days.

(21) Appl. No.: 16/729,014

(22) Filed: Dec. 27, 2019

(65) Prior Publication Data

US 2020/0171108 A1    Jun. 4, 2020

Related U.S. Application Data

(63) Continuation of application No. 15/237,496, filed on Aug. 15, 2016, now Pat. No. 10,517,908.

(60) Provisional application No. 62/204,915, filed on Aug. 13, 2015.

(51) Int. Cl.
| | | |
|---|---|---|
| *A61K 35/76* | (2015.01) | |
| *C12N 7/00* | (2006.01) | |
| *A61L 15/40* | (2006.01) | |
| *A01N 63/40* | (2020.01) | |

(52) U.S. Cl.
CPC .............. *A61K 35/76* (2013.01); *A01N 63/40* (2020.01); *A61L 15/40* (2013.01); *C12N 7/00* (2013.01); *C12N 2795/00021* (2013.01); *C12N 2795/00031* (2013.01); *C12N 2795/00032* (2013.01)

(58) Field of Classification Search
None
See application file for complete search history.

(56) References Cited

U.S. PATENT DOCUMENTS

| 8,388,946 | B2 | 3/2013 | Soothill et al. |
| 8,475,787 | B2 | 7/2013 | Harper |
| 9,623,058 | B2 | 4/2017 | Jia |
| 10,517,908 | B2 | 12/2019 | Shaw et al. |
| 2015/0216179 | A1 | 8/2015 | Jia |

(Continued)

FOREIGN PATENT DOCUMENTS

| WO | WO 2005/009451 | 2/2005 |
| WO | WO 2008/110840 | 9/2008 |

(Continued)

OTHER PUBLICATIONS

Ampliphi, AmpliPhi Biosciences reports favorable final results from Phase 1 Trial of AB-SA01 in chronic rhinosinusitis patients, 2016, 3 pages.

(Continued)

*Primary Examiner* — Michelle S Horning
(74) *Attorney, Agent, or Firm* — Mintz, Levin, Cohn, Ferris Glovsky and Popeo, P.C.

(57) ABSTRACT

The present invention relates to a bacteriophage composition comprising one or more (suitably two or more, or three) bacteriophages selected from Sa87, J-Sa36, Sa83, J-Sa37, or mutants thereof, use of the same for medical or non-medical applications, kits, bandage, and wound dressing comprising the same.

22 Claims, 1 Drawing Sheet

(56) References Cited

U.S. PATENT DOCUMENTS

| | | | |
|---|---|---|---|
| 2017/0065649 A1 | 3/2017 | Shaw | |
| 2018/0289756 A1 | 10/2018 | Harper et al. | |
| 2019/0359947 A1* | 11/2019 | Shaw | C12N 7/00 |
| 2021/0077551 A1* | 3/2021 | Morales | A61K 31/43 |

FOREIGN PATENT DOCUMENTS

| | | |
|---|---|---|
| WO | WO 2009/044163 | 4/2009 |
| WO | WO 2013/164640 | 11/2013 |
| WO | 2018146437 A1 | 8/2018 |

OTHER PUBLICATIONS

Attwood, The Babel of Bioinformatics, Science, 2000, pp. 471-473, vol. 290, No. 5491.

Anzctr, A Phase 1 Investigator Initiated Study to Evaluate the Safety, Tolerability and Preliminary Effectiveness of AB-SA01 in Patients with Chronic Rhinosinusitis Associated with *Staphylococcus aureus* Infection, 2016, 3 pages.

Baker, et al., Protein Structure Prediction and Structural Genomics, Science, 2001, pp. 93-96, vol. 294, No. 5540.

Barr, et al., Value of charcoal media for recovering staphylococci incorporated in Mupirocin ointment, J. Clin. Pathol., 1987, pp. 372-376, vol. 40.

Bautz, APHB: Early signs of efficacy seen in Phase 1 Trial of AB-SA01 in chronic rhinosinusitis, 2016, 4 pages.

Bautz, APHB: Safety of AB-SA01 firmly established following Phase 1 Trials, 2016, 3 pages.

Carlson, Appendix: Working with Bacteriophages: Common Techniques and Methodological Approaches, CRC Press, 2005, 58 pages.

European Patent Office, International Search Report and Written Opinion for PCT/GB2017/050376, dated Sep. 15, 2017, 16 pages.

Hyman, et al., Practical Methods for Determining Phage Growth Parameters, Cha. 18 In: Bacteriophages: Bacteriophages: Methods and Protocols, vol. 1:Isolation, Characterization, and Interactions, Clokie, M. R. J. et al. (eds.), 2009, pp. 175-202, vol. 501.

Kelly, et al., Development of a broad-host-range phage cocktail for biocontrol, Bioengineered Bugs, 2:1, 2011, pp.

Shaw, Efficacy of a bacteriophage cocktail in a *Staphylococcus aureus* mouse pneumonia model is comparable to Vancomycin, 2017, 1 page.

Thompson, Clustal W: Improving the sensitivity of progressive multiple sequence alignment through sequence weighing, position-specific gap penalties and weight matrix choice, Nucleic Acids Research, 1994, pp. 4673-4680, vol. 22, No. 22.

Walle, Align-m-A New Algorithm for Multiple Alignment of Highly Divergent Sequences, Bioinformatics, 2004, pp. 1428-1435, vol. 20, No. 9.

World Health Organization, International Clinical Trials Registry Platform, a phase 1 investigator initialed study to evaluate the safety, tolerability and preliminary effectiveness of AB-SA01 in patients with chronic rhinosinusitis associated with *Staphylococcus aureus* infection, 2017, 3 pages.

Trial Registered on Anzctr, Registration No. ACTRN12616000002482, Australian New Zealand Clinical Trials Registry, [Online], Dec. 14, 2016, [Retrieved on Jan. 22, 2021], <URL:https://anzctr.org.au/trial/registration/trialreview.aspx?actrn=12616000002482>.

Molecular Respiratory Disease, 2004, 8(4):331-333.

Darling et al. (2004) "Mauve: Multiple Alignment of Conserved Genomic Sequence With Rearrangements", Genome Res., 14(7):1394-1403.

Lehman et al. (2019) "Design and Preclinical Development of a Phage Product for the Treatment of Antibiotic-Resistant *Staphylococcus aureus* Infections", Viruses, 11 (88):16 pages.

Magiorakos et al. (Mar. 2012) "Multidrug-Resistant, Extensively Drug-Resistant and Pandrug-Resistant Bacteria: An International Expert Proposal for Interim Standard Definitions for Acquired Resistance", Clinical Microbiology and Infection, 18(3):268-281.

Otter et al. (2010) "Molecular epidemiology of community-associated meticillin-resistant *Staphylococcus aureus* in Europe", Lancet, 10(4):227-239.

Zhang et al. (Mar. 1, 2018) "Bacteriophage Effectively Kills Multidrug Resistant *Staphylococcus aureus* Clinical Isolates from Chronic Rhinosinusitis Patients", International Forum of Allergy & Rhinology, 8(3):406-414.

* cited by examiner

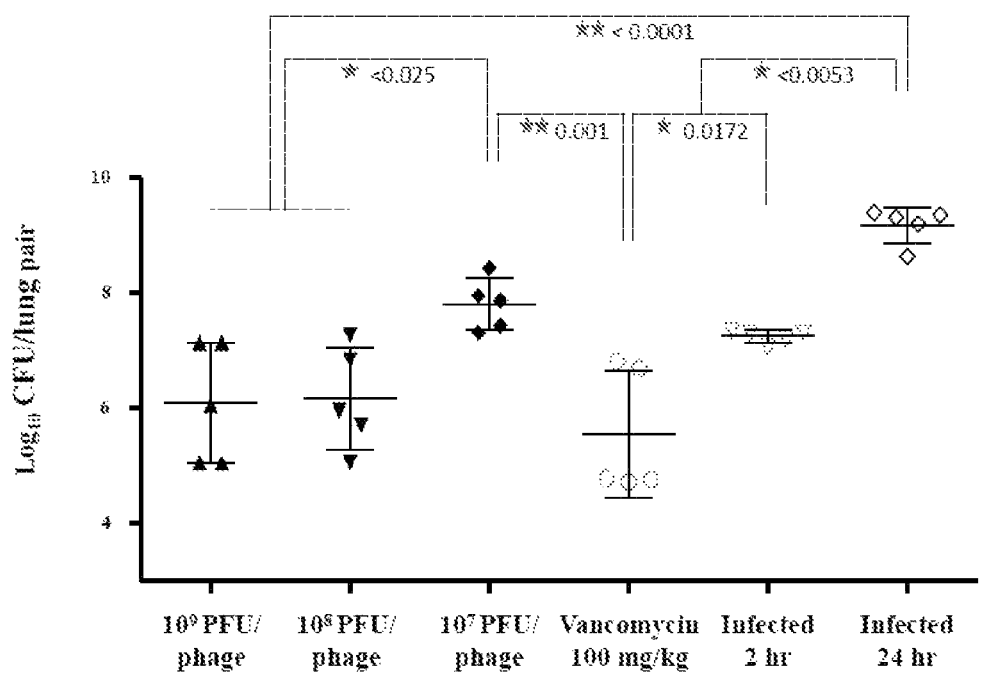

THERAPEUTIC BACTERIOPHAGE COMPOSITIONS

CROSS-REFERENCED APPLICATIONS

This application is a continuation of U.S. Ser. No. 15/237,496, filed Aug. 15, 2016, which claims priority benefit to U.S. Provisional 62/204,915 filed Aug. 13, 2015, which are incorporated by reference herein in their entireties.

FIELD OF THE INVENTION

The present invention relates to compositions of bacteriophages, and use of the same for medical and non-medical applications.

BACKGROUND

The rising tide of human pathogens that are resistant to antibiotics has created an urgent need for new treatments for serious bacterial infections. Novel approaches that circumvent traditional mechanisms of antibiotic resistance, can be effective against biofilms, and avoid disruption of the native gut flora are especially desirable. This clinical challenge has sparked renewed interest in bacteriophage (phage) therapy. Demonstration of efficacy in an animal model of infection is a preliminary step in the development of a new therapeutic agent.

SUMMARY OF THE INVENTION

In one aspect the present invention provides a bacteriophage composition comprising one or more bacteriophages selected from Sa87, J-Sa36, Sa83, J-Sa37, or mutants thereof.

In another aspect there is provided a bacteriophage composition of the invention for use as a medicament. Corresponding methods of treating a disease comprising administration of the bacteriophage composition to a subject are also provided.

In a further aspect the invention provides a bacteriophage composition of the invention for use in treating a pulmonary bacterial infection in a subject, wherein the bacteriophage composition is administered to the subject, and wherein the bacterial infection comprises *Staphylococcus aureus*.

The invention provides in one aspect use of a bacteriophage composition of the invention in the manufacture of a medicament for use in treating a pulmonary bacterial infection in a subject, wherein the bacteriophage composition is administered to the subject, and wherein the bacterial infection comprises *Staphylococcus aureus*.

In another aspect there is provided a method of treating a pulmonary bacterial infection in a subject comprising administering the bacteriophage composition of the invention to the subject, wherein the bacterial infection comprises *Staphylococcus aureus*.

In one aspect there is provided a kit comprising: a bacteriophage composition according to the invention; and instructions for use of same.

The invention provides a method of killing *Staphylococcus aureus* bacteria on a surface, said method comprising applying a bacteriophage composition of the invention to the surface.

In another aspect there is provided use of the bacteriophage composition or kit according to the invention for a non-medical application.

In a further aspect there is provided a bandage or wound dressing comprising a bacteriophage composition of the invention.

BRIEF DESCRIPTION OF THE DRAWINGS

Embodiments of the invention will now be described, by way of example only, with reference to the accompanying drawing, in which:

FIG. 1 shows efficacy of a phage cocktail vs. vancomycin in a *S. aureus* pneumonia model: statistical analysis of dosage groups. Statistical analysis was performed using Tukey's multiple comparisons test (Graphpad Prism 6, La Jolla, Calif.). Only groups demonstrating a significant difference in the pairwise comparisons are shown ($p<0.05$). Where two groups are compared to a third, the p value presented is the higher of the two pairwise comparisons. **$p$ 0.001, *$p$ 0.05.

DETAILED DESCRIPTION

The invention is predicated upon the surprising finding by the present inventors that a bacteriophage composition comprising one or more (preferably at least two) bacteriophages selected from Sa87, J-Sa36, Sa83, J-Sa37, or mutants thereof, is particularly advantageous for use in both medical and non-medical applications, and particularly for treating a pulmonary bacterial infection in a subject.

In one embodiment a bacteriophage composition comprises at least two bacteriophages selected from Sa87, J-Sa36, Sa83, J-Sa37, or mutants thereof. In one embodiment a bacteriophage composition comprises at least three bacteriophages selected from Sa87, J-Sa36, Sa83, J-Sa37, or mutants thereof. In another embodiment a bacteriophage composition comprises Sa87, J-Sa36, Sa83 or mutants thereof. Suitably a bacteriophage composition may comprise Sa87, J-Sa36, and Sa83. In one embodiment a bacteriophage composition consists essentially of Sa87, J-Sa36, and Sa83 or mutants thereof. Suitably a bacteriophage composition consists essentially of Sa87, J-Sa36, and Sa83.

The term "consists essentially of" as used herein means that only the bacteriophage(s) explicitly indicated are present in the bacteriophage composition, but that said composition may also contain a further non-bacteriophage constituent, such as an appropriate carrier, diluent, etc.

The term "mutant" as used herein refers to a bacteriophage differing genetically from Sa87, J-Sa36, Sa83, or J-Sa37 by one or more nucleotides but still retaining the ability to infect and lyse *Staphylococcus aureus* target bacteria. In one embodiment (alternatively or additionally) a "mutant" bacteriophage is capable of lysing the same target bacterial strains as Sa87, J-Sa36, Sa83, and/or J-Sa37, and further capable of lysing one or more additional bacterial strains. In one embodiment a mutant may have at least 75%, 80%, 85%, 90%, 95% or 99% sequence identity across its entire genome when compared to Sa87, J-Sa36, Sa83, or J-Sa37 (suitably when compared to Sa87, J-Sa36 or Sa83).

Any of a variety of sequence alignment methods can be used to determine percent identity, including, without limitation, global methods, local methods and hybrid methods, such as segment approach methods. Protocols to determine percent identity are routine procedures within the scope of one skilled in the art. Global methods align sequences from the beginning to the end of the molecule and determine the best alignment by adding up scores of individual nucleotide pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement. Non-limiting methods include, e.g., BLAST, Match-box, see, e.g., Align-M, see, e.g., Ivo Van Walle et al., Align-M—A New Algorithm for Multiple Alignment of Highly Divergent Sequences, 20(9) Bioinformatics: 1428-1435 (2004).

The bacteriophage composition of the invention targets one or more *Staphylococcus aureus* strains. In one embodiment a *Staphylococcus aureus* strain targeted is a methicillin-resistant *Staphylococcus aureus* (MRSA).

The bacteriophages of a composition of the invention may be provided in the form of a single therapeutic composition (preferred) or as a number of separate compositions each comprising one or more members of the composition. In embodiments where the bacteriophages are provided in a number of separate compositions, said bacteriophages may be administered to a subject sequentially or simultaneously.

A bacteriophage for inclusion in a composition of the invention may be propagated by any suitable method known in the art. For example one or more bacteriophage(s) may be grown separately in host bacterial strains capable of supporting growth of the bacteriophage. Typically, the bacteriophage will be grown in said host bacterial strain to high concentrations, titrated and combined to form a composition of the invention.

The amount of each bacteriophage employed (e.g. in a bacteriophage composition, method or use of the invention) will depend upon its virulence against the target bacterial species. Typically, said one or more bacteriophage(s) may be combined to form a composition comprising at least about $1 \times 10^7$, $1 \times 10^8$, $1 \times 10^9$ or $1 \times 10^{10}$, or $1 \times 10^{11}$ plaque forming units (PFU) of each phage per ml of composition. Suitably, said one or more bacteriophage(s) may be combined to form a composition comprising at least about $1 \times 10^8$ or $1 \times 10^9$ PFU of each phage per ml of composition.

When selecting bacteriophages for inclusion in a composition of the invention, the methods taught in WO 2013/164640 A1 (incorporated herein by reference) may be used. In one embodiment said method comprises: a. providing two or more different bacteriophages, wherein each of said two or more different bacteriophages independently retards growth of a *Staphylococcus aureus* species or strain; b. combining at least two of said two or more different bacteriophages; and c. determining growth of the *Staphylococcus aureus* species or strain in the presence of said combination of two or more different bacteriophages, wherein the *Staphylococcus aureus* species or strain growth conditions are the same or equivalent in steps a. and c.; d. wherein, if said combination retards growth of the *Staphylococcus aureus* species or strain at least equal to the greatest growth retardation achieved independently by any one of said two or more different bacteriophages, the combination is accepted as a composition of bacteriophages; and e. wherein, if said combination retards growth of the target bacterial species or strain less than the greatest growth retardation achieved independently by any one of said two or more different bacteriophages, the combination is initially rejected as a composition of bacteriophages.

The present inventors surprisingly found that by employing a method of the foregoing embodiment, an improved bacteriophage composition having bacteriophages Sa87, J-Sa36 and Sa83 (and optionally mutants thereof) was obtained. Advantageously, said bacteriophage composition exhibits improved therapeutic efficacy against *Staphylococcus aureus* when compared to conventional bacteriophage compositions and/or a composition comprising bacteriophages Sa87, J-Sa36, Sa83, and J-Sa37 (and optionally mutants thereof). Thus, a preferred bacteriophage composition comprises or consists essentially of Sa87, J-Sa36 and Sa83.

In some embodiments a bacteriophage composition of the present invention may further comprise one or more additional bacteriophages. Said one or more additional bacteriophages may target a *Staphylococcus aureus* species or strain, or a different bacterial target, for example selected from one or more of the following genera *Staphylococcus, Helicobacter, Klebsiella, Listeria, Mycobacterium, Escherichia, Meningococcus, Campylobacter, Streptococcus, Enterococcus, Shigella, Pseudomonas* (e.g. *Pseudomonas aeruginosa*), *Burkholderia, Clostridium, Legionella, Acetinobacter, Salmonella*, or combinations thereof.

The one or more additional bacteriophages may be one taught in WO 2009/044163 (incorporated herein by reference), a bacteriophage K and/or bacteriophage P68 described therein.

In one embodiment a bacteriophage composition comprises one or more (preferably at least two) bacteriophages selected from Sa87, J-Sa36, Sa83, J-Sa37, or mutants thereof, and a pharmaceutically acceptable carrier, diluent, excipient or combinations thereof. Suitable carriers, diluents and/or excipients may include isotonic saline solutions, such as phosphate-buffered saline.

A bacteriophage composition of the invention may be formulated as a disinfectant composition. The disinfectant composition may be in the form of a spray or liquid wash for a surface. The composition may be a band wash. Suitably where the composition is a formulation for topical application, it may take the form of a lotion, cream, ointment, paste, gel, foam, or any other physical form as a carrier generally known for topical administration. Such thickened topical formulations are particularly advantageous because the formulations adhere to the area of the skin on which the material is placed, thus allowing a localised high concentration of bacteriophages to be introduced to the particular area to be disinfected. For example, paraffin- and lanolin-based creams, which are particularly useful for the application of product to the nasal cavity, are generally known in the art. However, other thickeners, such as polymer thickeners, may be used. The formulations may also comprise one or more of the following: water, preservatives, active surfactants, emulsifiers, anti-oxidants, or solvents.

A bacteriophage composition of the invention may be formulated for nasal, oral, parenteral, intramuscular, intravenous, subcutaneous, transdermal, ocular or aural administration. Such a bacteriophage preparation may be used directly, stored frozen in aqueous or other solution with an appropriate cryoprotectant (e.g. 10% sucrose), freeze dried and rehydrated prior to use, or rendered stable in some other formulation including (but not limited to) tablet, emulsion, ointment, or impregnated wound dressing or other item. For embodiments directed to the treatment of a pulmonary bacterial infection, the bacteriophage composition may be formulated for pulmonary delivery via nasal or oral administration (e.g. by aerosolisation of the bacteriophage composition). Thus, in one embodiment the bacteriophage composition may be comprised in a pulmonary delivery means, such as an inhaler or a respirator.

The present invention further relates to the use of a bacteriophage composition herein as a medicament (e.g. for treating a *Staphylococcus aureus* infection). Suitably, the bacteriophage composition finds particular use in treating a pulmonary bacterial infection, wherein the bacterial infection comprises (or consists of) Staphylococcus aureus. A bacteriophage composition comprising or consisting essentially of Sa87, J-Sa36, Sa83, or mutants thereof is particularly advantageous when treating a Staphylococcus aureus infection (e.g. pulmonary infection).

The term "treating" as used herein is intended to encompass prophylactic treatment as well as corrective treatment (treatment of a subject already suffering from a disease). Preferably "treating" refers to corrective treatment.

A use or method of the invention typically comprises administering a bacteriophage composition described herein to a subject. As used herein, a "subject" is a mammal, such as a human or other animal. In one embodiment the subject is a human subject with a Staphylococcus aureus infection (e.g. a Staphylococcus aureus pulmonary infection).

In one embodiment a bacteriophage composition is administered to a subject at a dosage of at least about $1 \times 10^7$ PFU of each phage or at least about $5 \times 10^7$ PFU of each phage. Suitably, the bacteriophage composition may be administered at a dosage of at least about $1 \times 10^8$ PFU of each phage or at least about $1 \times 10^9$ PFU of each phage. A suitable dosage range may be between about $1 \times 10^7$ PFU of each phage to about $1 \times 10^{11}$ PFU of each phage, preferably between about $5 \times 10^7$ PFU of each phage to about $5 \times 10^9$ PFU of each phage.

In some embodiments the bacteriophage composition is administered at least once, twice, three times, or four times daily. Suitably the bacteriophage composition may be administered twice daily. In one embodiment, therefore, a dosage of at least about $5 \times 10^7$ PFU of each phage is administered at least once, twice, three times, or four times daily. In another embodiment at least about $1 \times 10^8$ PFU of each phage is administered at least once, twice, three times, or four times daily. In a further embodiment at least about $1 \times 10^9$ PFU of each phage is administered at least once, twice, three times, or four times daily. Suitably a dosage range between about $1 \times 10^7$ PFU of each of phage to about $1 \times 10^{11}$ PFU of each of phage may be administered at least once, twice, three times, or four times daily. Preferably a dosage range between about $5 \times 10^7$ PFU of each of phage to about $5 \times 10^9$ PFU of each of phage may be administered at least once, twice, three times, or four times daily.

A bacteriophage composition for use as a medicament may be administered by any route selected on the basis of the condition to be treated. In one embodiment the route of administration is nasal, oral, pulmonary, parenteral, intramuscular, intravenous, subcutaneous, transdermal, ocular, aural or combinations thereof. When used in the treatment of a pulmonary bacterial infection, the bacteriophage composition may be administered nasally or orally, for example via aerosolisation using an appropriate pulmonary delivery means, such as an inhaler or respirator.

In one embodiment an antibiotic (suitably a chemical antibiotic) may be administered in combination with the bacteriophage composition of the invention. Combinatorial administration of antibiotics and bacteriophages is taught in WO 2008/110840 and WO 2005/009451, which teaching is incorporated herein by reference. The antibiotic may be administered simultaneously or sequentially with the bacteriophage composition. Suitably, the one or more antibiotics may be administered after the composition such that bacteriophage replication has become established before antibiotic treatment begins. In this case, antibiotic treatment may be delayed for one or more hours or days from application of the one or more bacteriophages, e.g. from 1 to 2, 3, 4, 5, 6, 7, 8, 9 or 10 days. Where a bacteriophage composition comprising a plurality of bacteriophages is employed with each member of the composition exhibiting different strain specificity, it will suffice that at least a proportion (e.g. one or more bacteriophage(s)) of the composition is capable of targeting the bacterial infection.

Thus, in some embodiments a bacteriophage composition comprises one or more antibiotics, such as one or more chemical antibiotics. An antibiotic may be selected based on sensitivity of a Staphylococcus aureus species or strain to said antibiotic. Suitably the Staphylococcus aureus species or strain may be the same species or strain present in a subject to be treated. In one embodiment a Staphylococcus aureus species or strain is taken from a subject to be treated and tested for antibiotic sensitivity. Sensitivity may be determined by in vitro sensitivity assays known in the art.

Alternatively or additionally, an antibiotic may be selected because it is known to be active against a bacteria known to be (or thought likely to be) present together with a Staphylococcus aureus infection to be treated (e.g. as part of a bacterial biofilm).

In one embodiment an antibiotic is one or more selected from: vancomycin, teicoplanin, penicillin, methicillin, flucloxacillin, dicloxacillin, cephalosporins (e.g. cefazolin, cephalothin, cephalexin), clindamycin, lincomycin, erythromycin, or combinations thereof. Suitably the antibiotic may be vancomycin and/or teicoplanin.

In one embodiment a use or method of the invention comprises: a. administration of a bacteriophage composition to a subject in vivo; b. in vitro monitoring of the sensitivity of a sample of bacterial cells from an infection (e.g. present in the subject) or from another infection by the same strain to one or more antibiotic(s); and c. administration of said one or more antibiotic(s), when it has been established that said sensitivity to said one or more antibiotic(s) has been induced.

In one embodiment the antibiotic (e.g. chemical antibiotic) is administered at a time period at which sensitivity of sampled bacteria to the antibiotic is induced by the composition. In some embodiments the time period may be at least 12, 24 or 48 hours. In other embodiments the bacteriophage composition and the antibiotic may be administered at intervals of one day to two months apart, preferably at intervals of one to four weeks apart, suitably at intervals of two weeks apart.

In one embodiment an antibiotic is administered at a dose of at least 50, 100 or 150 mg/kg once or twice daily. Suitably an antibiotic may be administered at a dose of 100 mg/kg once or twice daily.

In one embodiment a bacteriophage composition may be used in a method of killing Staphylococcus aureus bacteria on a surface, said method comprising applying a bacteriophage composition of the invention (e.g. formulated as a disinfectant composition) to the surface. Suitably, the surface is a site of contamination or prospective site of contamination.

In one embodiment the surface is the skin of a mammal (e.g. a human), for example a nasal cavity. Alternatively or additionally, the surface may be equipment (suitably medical equipment), bedding, furniture, walls or floors (e.g. in a clinical environment).

Suitably, a bacteriophage composition may be applied to a surface at a ratio of at least 4:1, 5:1, 6:1, 7:1, 8:1, 9:1, 10:1, at least 20:1, 40:1, 50:1, at least 100:1 PFU of (suitably each) bacteriophage to colony forming units (CFU) of bacteria.

The present invention also provides a kit comprising: a bacteriophage composition according to the invention; and instructions for use of same (e.g. in medicine). The kit may further comprise an antibiotic (e.g. a chemical antibiotic) and instructions for use of same in combination with the bacteriophage composition.

In one embodiment the instructions provide details for dosing a bacteriophage composition of the invention as described herein. In one embodiment the instructions included in a kit of the invention are for use of same in treating a Staphylococcus aureus infection, e.g. a pulmonary infection.

The invention contemplates use of a bacteriophage composition or kit of the invention for non-medical applications. For example a bacteriophage composition or kit may be used in food hygiene, agriculture or crop protection, and/or in environmental hygiene applications. Thus, in one embodiment the kit comprises instructions for use of a bacteriophage composition in a non-medical application.

A bacteriophage composition of the invention may also be comprised in a bandage or wound dressing. The wound dressing may be a pad or sticking plaster-type dressing. The bacteriophages may be applied to the wound dressing or bandage as a disinfectant formulation or topical cream, prior to applying to the wound dressing or bandage. Alternatively, the wound dressing or bandage may be soaked in a carrier containing the bacteriophages and dried to impregnate said bacteriophages within the dressing or bandage. Bacteriophages may also be adsorbed onto the surface of the bandage or wound dressing using techniques generally known in the art. The advantage of this approach is that the bandage or wound dressing allows the bacteriophages to be brought into contact with a wound which may contain the bacteria. In a related aspect, the present invention also provides methods of inhibiting or treating bacteria by applying a bandage or wound dressing to a subject.

The bacteriophage composition of the present invention is particularly advantageous for use in medicine, and shows clinical efficacy in the treatment of Staphylococcus aureus infections. For example, it has surprisingly been found that said bacteriophage composition is particularly suited to treatment of Staphylococcus aureus pulmonary infections.

Additionally, the bacteriophage composition of the invention is efficacious against a broad spectrum of Staphylococcus aureus strains.

A combination of a bacteriophage composition and an antibiotic (e.g. a chemical antibiotic) may provide an enhanced (e.g. synergistic) therapeutic showing unexpectedly improved efficacy when treating a Staphylococcus aureus infection, particularly when used in treating a pulmonary Staphylococcus aureus infection.

A bacteriophage composition comprising or consisting essentially of Sa87, J-Sa36, and Sa83 (optionally further including one or more mutants thereof) surprisingly exhibits reduced bacteriophage antagonism and/or reduces development of resistance in Staphylococcus aureus target bacteria. Surprisingly, said bacteriophage composition exhibits reduced bacteriophage antagonism and/or reduces development of resistance in Staphylococcus aureus target bacteria when compared to a composition comprising or consisting essentially of Sa87, J-Sa36, Sa83, and J-Sa37 (optionally further including one or more mutants thereof).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. The headings provided herein are not limitations of the various aspects or embodiments of this disclosure which can be had by reference to the specification as a whole. Accordingly, the terms defined immediately below are more fully defined by reference to the specification as a whole.

Other definitions of terms may appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a bacteriophage composition" includes a plurality of such candidate agents and reference to "the bacteriophage" includes reference to one or more bacteriophages and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following FIGURE and Examples.

EXAMPLES

Example 1 Assembly of Bacteriophage Cocktail

In some embodiments, a cocktail of four bacteriophages Sa87, J-Sa36, J-Sa37 and Sa83, which together had broad activity against a panel of recent diverse S. aureus clinical isolates (unpublished data), was used for animal studies. In an exemplary method, phage lysates were prepared using manufacturing hosts SPS1216 and SPS1226, which do not release endogenous prophage during the production cycle. Cultures were grown in bioreactors to an $OD_{600}$ 0.2 prior to phage addition. Incubation at 37° C. was continued and absorbance read at least every 60 minutes. Cultures were harvested after bacterial lysis, and impurities separated from the phages with several filtration steps followed by chromatographic steps that enabled reduction of debris such as host cell proteins and host cell DNA. After purification, lysates were additionally concentrated using spin columns (Amicon® Ultra 15-100 kDa, Merck Millipore, Darmstadt, Germany) such that final phage titers were $1\times10^{11}$ PFU/mL. At the end of the process, buffer was exchanged and all material was filter-sterilized (0.22 μm filter) and stored at 2-8° C. Plaque assays were used to titer the phage stocks (Carlson, K., In E. Kutter and A. Sulakvelidze (ed.), Bacteriophages: Biology and Application, (2005) 437-494, CRC Press, Boca Raton, Fla., Hyman, P., et al., Meth. Mol. Biol. (2009) 501:175-202). The four purified phage samples were combined such that each phage was present in the final cocktail at a concentration of $2\times10^{10}$ PFU/mL per phage and then additionally diluted 1:10 or 1:100 to obtain the 3 dosing solutions. Final endotoxin levels were <1000 EU/mL, which was acceptable for animal studies.

Example 2 Bacterial Strains

In a non-limiting example, *Staphylococcus aureus* UNT109-3 and UNT144-3 used for this study are part of the UNT culture collection. Frozen stocks were inoculated into TRIPTICASE™ SOY BROTH (Triptic Soy Broth) (BBL™ Laboratories)+5% defibrinated sheep blood (TSBb) and incubated for 18 hrs at 37° C. (shaking). After 18 hrs the culture was diluted 1:10 into fresh TSBb and incubated for a further 5 hrs before being diluted in fresh TSB for inoculation into the mice.

Example 3 Assessment of *S. aureus* Virulence in the Murine Pneumonia Model

In a non-limiting example, the sensitivity of two *S. aureus* clinical isolates, UNT109-3 (NRS234, native valve endocarditis) and UNT144-3, that have been previously utilized in animal models of infection, was evaluated vs. the individual phage and the 4-phage cocktail. In some embodiments, both strains were fully sensitive to the cocktail as well as the individual phage Sa87, J-Sa36, and Sa83. Phages Sa87, J-Sa36, and Sa83 demonstrated improved efficacy against UNT109-3 when compared to phage J-Sa37. The virulence of the two strains was then evaluated in the murine lung infection model. Female Hsd:ICR(CD-1) mice (Harlan Laboratories, Houston, Tex.) were administered 150 and 100 mg/kg cyclophosphamide on day −4 and day −1 prior to infection to render them neutropenic. Groups of 5 mice were then anaesthetized by intraperitoneal (IP) injection of 0.15 mL of a mixture of ketamine HCl (100 mg/kg body weight) plus xylazine (10 mg/kg body weight). Once anaesthetized, mice were infected intranasally by placing drops on the external nares and allowing inhalation of the 50 μl inoculum. Twenty-four hours after infection, mice were euthanized by $CO_2$ inhalation and lungs processed for bacterial titers. Bacterial counts were enumerated on Brain Heart Infusion agar (Difco™ Laboratories)+0.5% activated charcoal (Sigma-Aldrich) plates for ease of recovering and detecting *S. aureus* (Barr, J. G., et al., *J Clin. Pathol.* (1987) 40:372-376). Mice that had received 7.13 $\log_{10}$ CFU of strain UNT109-3 all succumbed to the infection prior to the 24-hour harvest, indicating unsuitable virulence. All mice infected with 6.95 log o CFU of strain UNT144-3 survived until sampling, and exhibited mean log o CFU/lung pair titers of 6.78±0.34 and 8.17±0.91 and 2 and 24 hours post-infection, respectively. These data indicate that the virulence of the UNT144-3 strain, both in terms of lung titers and survival, is comparable to historical results obtained for other MRSA isolates (unpublished data). Based on these results, UNT144-3 was selected for use in the efficacy studies.

Example 4 Efficacy of the 4 Phage Cocktail in the *S. aureus* Pneumonia Model

In a non-limiting example, six groups of 5 mice were rendered neutropenic as described above. Once anaesthetized, an inoculum of 6.98 log o CFU in 50 μL of strain UNT144-3 was delivered intranasally, resulting in mean bacterial lung titers of 7.24 $\log_{10}$ CFU/lung pair at 2 hrs, which increased to 9.18 $\log_{10}$ CFU/lung pair at 24 hours in the untreated control group (FIG. 1). 100 mg/kg Vancomycin was administered as a subcutaneous injection 2 hr and 6 hr post-infection; PBS-Mg diluent was delivered intranasally at 2 hr and 6 hr post-infection to the untreated control group.

Three phage cocktail treatment groups were evaluated for efficacy: $2\times10^{10}$ PFU/mL per phage, $2\times10^9$ PFU/mL per phage, and $2\times10^8$ PFU/mL per phage. As described below, 50 μL doses of phage were administered at both 2 hr and 6 hr post-infection, such that each mouse received $1\times10^9$ PFU of each phage, $1\times10^8$ PFU of each phage, or $1\times10^7$ PFU of each phage at each time point, according to its dosage group. At the time of the first administration of 50 μL phage, the colony counts in the lung were 7.24 $\log_{10}$ CFU/lung pair. Thus, the multiplicity of infection was ~60, ~6 and ~0.6 for the 3 dosage groups at the 2 hr time point when the first phage dose was administered.

Administration of two doses of the phage cocktail resulted in *S. aureus* lung titers of 6.08, 6.16 and 7.8 $\log^{10}$ CFU/lung pair for the $1\times10^9$ PFU/phage, $1\times10^8$ PFU/phage, and $1\times10^7$ PFU/phage treatment groups, respectively. These correspond to 1.38-3.1 $\log_{10}$ CFU reductions compared to the 24 hr vehicle control group and 1.08-1.16 $\log_{10}$ CFU reductions for the $1\times10^9$ PFU/phage and $1\times10^8$ PFU/phage groups compared to bacterial titers at 2 hrs post-infection. FIG. 1 shows a comparison of the different treatment groups that demonstrated statistical significance as determined by ANOVA analysis (Tukey's multiple comparisons test). The $1\times10^9$ PFU/phage, $1\times10^8$ PFU/phage, treatment groups demonstrated a significant reduction in lung CFU vs the 24 hr non-treated control ($P<0.0001$ for both). Vancomycin administration (100 mg/kg SC at 2 and 6 hrs) resulted in 24 hour bacterial lung titers of 5.55 $\log_{10}$ CFU, similar to the two highest phage doses (no significant difference between those 3 groups was observed).

Example 5 Analysis of Colonies Resultinci from Mouse Luno Homocienates after Infection In a non-limiting example, a total of 27 *S. aureus* colonies recovered from the murine lung infection model were evaluated for sensitivity to the individual phage components (Sa83, Sa87, J-Sa36, J-Sa37) and to the 4-phage cocktail. Colonies from the 2 hr untreated cohort appeared homogenous on the BHI-charcoal plates; thus a single colony was isolated from each of 3 different mice. In some cases, both normal and translucent colonies were observed and therefore both colony types were evaluated from 3 different mice per group (e.g., 24 hr untreated and vancomycin groups). Four colonies from each of the three *S. aureus* morphotypes seen among phage-treated groups were also evaluated (total 12): these included colonies with a typical *S. aureus* morphology as well as translucent colonies. Spot tests were performed on lawns of the 27 recovered colonies in order to assess phage sensitivity to the 4 individual phage and the phage cocktail using 5 μL spots of the neat, $10^{-1}$, $10^{-2}$, $10^{-3}$, and $0^{-4}$ serial phage dilutions (Carlson, K., supra, Hyman, P., supra). Testing was performed in triplicate. Susceptible control strains (SPS1216 and SPS1226) were run in parallel. Bacteria were considered sensitive if a visible clearing of the bacterial lawn, that was attributable to productive phage infection, was observed (e.g., consistent scoring or progression to individual plaques in serial dilutions). The 27 colonies demonstrated equivalent sensitivity to UNT144-3 for the phage cocktail as well as three individual phage Sa83, Sa87 and J-Sa36.

In this study, we demonstrated that the efficacy of a phage cocktail at $1\times10^8$ PFU/phage (MOI of each phage ~6 at the time of the first dose) and $1\times10^9$ PFU/phage (MOI of each phage ~60 at the time of the first dose) was comparable to vancomycin dosed at 100 mg/kg SC. Additionally, the *S. aureus* isolates that were re-isolated from infected mice remained sensitive to the phage cocktail. These data provide a first step in the evaluation and development of a phage therapeutic, including initial assessment of the dosing regimen.

TABLE 1

*S. aureus* Neutropenic Lung Model

| Group | # Mice | Test Article | Route | Dose OR Titer (BID) | CFU Assessed (Time) |
|---|---|---|---|---|---|
| 1 | 5 | Phage | IN | 1e9 PFU/phage | 24 hr |
| 2 | 5 | | | 1e8 PFU/phage | |
| 3 | 5 | | | 1e7 PFU/phage | |
| 4 | 5 | Vancomycin | SC | 100 mg/kg | 24 hr |
| 5 | 5 | Untreated | — | — | 24 hr |
| 6 | 5 | | — | — | 2 hr |

TABLE 2

Evaluation of 4 phage cocktail vs vancomycin

| Dose OR Titer | CFU Assessed (Time) | Mean ± SD logo CFU/Lung Pair |
|---|---|---|
| 1e9 PFU/phage BID | 24 hr | 6.08 ± 1.04 |
| 1e8 PFU/phage BID | 24 hr | 6.16 ± 0.89 |
| 1e7 PFU/phage BID | 24 hr | 7.8 ± 0.45 |
| Vancomycin | 24 hr | 5.55 ± 1.1 |
| Infected, untreated | 24 hr | 9.18 ± 0.32 |
| Infected, untreated | 2 hr | 7.24 ± 0.12 |

Example 6 Assembly of a 3 Phage Bacteriophage Composition

A number of bacteriophages (including Sa87, J-Sa36, Sa83, and J-Sa37) targeting *Staphylococcus aureus* are grown on permissive host strains and then tested against a range of *S. aureus* strains by: spot testing on bacterial lawns, enumerative plaque assay and broth culture using a plate reader assay system. The plate reader monitors the optical density of a broth culture containing bacteriophages with a suitable host in a multi-well plate format. This latter method allows detailed kinetics of the infection process to be evaluated. Bacteriophages showing good plaque formation are selected.

Candidate bacteriophages are propagated in liquid (broth) culture and lysates prepared. Clarified lysates are purified by centrifugation through a sucrose cushion (27 ml of each lysate is carefully over-layered onto 5 ml of a sterile 10% w/v sucrose 'cushion', in 36 ml polypropylene tubes prior to centrifugation).

The individual bacteriophages (including Sa87, J-Sa36, Sa83, and J-Sa37) are then retested both individually at higher MOI (multiplicity of infection [ratio of infecting bacteriophage to bacterial host cells]) and as a mixture. The results of this testing are surprising, bacteriophages Sa87, J-Sa36, Sa83, J-Sa37 produce effective reduction of bacterial host numbers with very limited development of resistance when each bacteriophage is tested in isolation. However, when a mixture of all four bacteriophages (Sa87, J-Sa36, Sa83, J-Sa37) is used, development of resistant forms is more rapid than when the bacteriophages are used in isolation, indicating antagonistic effects in the mixed bacteriophage infection that permit enhanced bacterial escape.

Further testing clarifies that bacteriophage J-Sa37 appears to be antagonistic to the effects of bacteriophages Sa87, J-Sa36 and/or Sa83 in reducing the development of bacterial resistance (as is measured by optical density at OD600) illustrating the antagonistic effect of J-Sa37. An improved bacteriophage composition is provided having bacteriophages Sa87, J-Sa36 and Sa83 which demonstrates enhanced therapeutic efficacy when tested using the pneumonia model (see Examples 3-5).

Example 7 Preparation of Mutants of Sa87, J-Sa36 and Sa83

Bacteriophages Sa87, J-Sa36, and Sa83 are iteratively passaged with *S. aureus* strains using conventional techniques (see for example Kelly et al, (2011), Bioengineered Bugs, 2:1, 31-37, which is incorporated herein by reference). Escape phages capable of lysing *S. aureus* strains previously resistant are selected. Genetic mutation of said escape phages compared to bacteriophages Sa87, J-Sa36, and/or Sa83 is confirmed by genetic sequencing. The escape phages are selected for inclusion in a bacteriophage composition comprising Sa87, J-Sa36, and/or Sa83 based on the methodology of Example 6. The bacteriophage composition demonstrates similarly enhanced therapeutic efficacy to the composition having bacteriophages Sa87, J-Sa36, and Sa83 when tested using the pneumonia model (see Examples 3-5).

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

What is claimed:

1. A bacteriophage composition comprising at least two bacteriophages selected from Sa87, J-Sa36, and Sa83.

2. The bacteriophage composition of claim 1, comprising purified bacteriophages Sa87, J-Sa36, and Sa83.

3. A bacteriophage composition consisting essentially of Sa87, J-Sa36, and Sa83.

4. The bacteriophage composition of claim 1, further comprising an antibiotic.

5. The bacteriophage composition of claim 1, further comprising a pharmaceutically acceptable carrier, diluent, excipient or combinations thereof.

6. The bacteriophage composition of claim 2, wherein the composition comprises $1\times10^{11}$ PFU/mL per phage.

7. The bacteriophage composition of claim 6, wherein the composition has a final endotoxin level less than 1000 EU/mL.

8. The composition of claim 7, wherein the composition is diluted 1:10.

9. The composition of claim 7, wherein the composition is diluted 1:100.

10. The composition of claim 1, wherein the composition is administered to a mammal in a dosage range between about $1\times10^{7}$ to about $1\times10^{11}$ PFU of each phage at least once daily.

11. A bacteriophage composition comprising two or more purified bacteriophage populations selected from Sa87, J-Sa36, and Sa83.

12. The bacteriophage composition of claim 11, further comprising an antibiotic.

13. The bacteriophage composition of claim 11, further comprising a pharmaceutically acceptable carrier, diluent, excipient or combinations thereof.

14. The bacteriophage composition of claim 11, wherein the composition comprises $1\times10^{11}$ PFU/mL per phage.

15. The bacteriophage composition of claim 14, wherein the composition has a final endotoxin level less than 1000 EU/mL.

16. The composition of claim 15, wherein the composition is diluted 1:10.

17. The composition of claim 15, wherein the composition is diluted 1:100.

18. The composition of claim 15, wherein the composition is administered to a mammal in a dosage range between about $1\times10^{7}$ to about $1\times10^{11}$ PFU of each phage at least once daily.

19. A kit comprising:
  a. a bacteriophage composition according to claim 1; and
  b. instructions for use of same.

20. The kit of claim 19, further comprising an antibiotic and instructions for use of same in combination with the bacteriophage composition.

21. The kit of claim 20, wherein said instructions are for use of same in treating a *Staphylococcus aureus* infection.

22. The kit of claim 21, wherein the *Staphylococcus aureus* infection is a pulmonary infection.

* * * * *